United States Patent [19]
Pape et al.

[11] Patent Number: 6,141,583
[45] Date of Patent: Oct. 31, 2000

[54] IMPLANTABLE MEDICAL DEVICE INCORPORATING PERFORMANCE BASED ADJUSTABLE POWER SUPPLY

[75] Inventors: Forrest C. M. Pape, New Brighton; Carl A. Schu, Plymouth, both of Minn.

[73] Assignee: Medtronic, Inc., Minneapolis, Minn.

[21] Appl. No.: 09/247,458

[22] Filed: Feb. 9, 1999

[51] Int. Cl.$^7$ ..................................................... A61N 1/08

[52] U.S. Cl. ............................................... 607/2; 607/16

[58] Field of Search ................................. 607/16, 2, 9, 4, 607/5, 60, 34; 600/509, 518, 300

[56] References Cited

U.S. PATENT DOCUMENTS

| | | | |
|---|---|---|---|
| 4,273,133 | 6/1981 | Hartlaub et al. | 607/30 |
| 4,693,253 | 9/1987 | Adams | 128/419 D |
| 4,830,006 | 5/1989 | Haluska et al. | 128/419 PG |
| 4,932,407 | 6/1990 | Williams | 128/419 D |
| 4,971,058 | 11/1990 | Pless et al. | 128/419 PG |
| 5,127,404 | 7/1992 | Wyborney et al. | 128/419 P |
| 5,265,588 | 11/1993 | Nelson et al. | 607/5 |
| 5,312,441 | 5/1994 | Mader et al. | 607/5 |
| 5,827,326 | 10/1998 | Kroll et al. | 607/5 |
| 5,924,979 | 7/1999 | Swedlow et al. | 600/300 |
| 5,939,998 | 8/1999 | Caporuscio et al. | 340/825.08 |

*Primary Examiner*—Kennedy Schaetzle
*Attorney, Agent, or Firm*—Reed A. Duthler; Harold R. Patton

[57] ABSTRACT

A method or apparatus for conserving power in an implantable medical device (IMD) of the type having at least one IC powered by a battery wherein, in each such IC, a voltage dependent oscillator for providing oscillator output signals at an oscillation frequency dependent upon applied supply voltage to the IC is incorporated into the IC. The voltage dependent oscillator oscillates at a frequency that is characteristic of the switching speed of all logic circuitry on the IC die that can be attained with the applied supply voltage. The applied supply voltage is regulated so that the oscillation frequency is maintained at no less than a target or desired oscillation frequency or within a desired oscillation frequency range. The power supply voltage that is applied to the IC is based directly on the performance of all logic circuitry of the IC. In order to provide the comparison function, the oscillator output signals are counted, and the oscillator output signal count accumulated over a predetermined number of system clock signals is compared to a target count that is correlated to the desired oscillation frequency. The counts are compared, and the supply voltage is adjusted upward or downward or is maintained the same dependent upon whether the oscillator output signal count falls below or rises above or is equal to the target count, respectively. The supply voltage adjustment is preferably achieved employing a digitally controlled power supply by calculating a digital voltage from the comparison of the oscillator output signal count to the target count, and storing the digital voltage in a register of the power supply.

19 Claims, 5 Drawing Sheets

IMPLANTABLE MEDICAL DEVICE INCORPORATING PERFORMANCE BASED ADJUSTABLE POWER SUPPLY

FIELD OF THE INVENTION

This invention relates generally to implantable body tissue stimulating apparatus, and more particularly to an improved power supply for integrated circuits (ICs) controlling the operations thereof.

BACKGROUND OF THE INVENTION

A wide variety of implantable medical devices (IMDs) that employ electronic circuitry for providing electrical stimulation of body tissue and/or monitoring a physiologic condition are known in the art. A number of IMDs of various types are known in the art for delivering electrical stimulating pulses to selected body tissue and typically comprise an implantable pulse generator (IPG) for generating the stimulating pulses under prescribed conditions and at least one lead bearing a stimulation electrode for delivering the stimulating pulses to the selected tissue. For example, cardiac pacemakers and ICDs have been developed for maintaining a desired heart rate during episodes of bradycardia or for applying cardioversion or defibrillation therapies to the heart upon detection of serious arrhythmias. Other nerve, brain, muscle and organ tissue stimulating medical devices are also known for treating a variety of conditions.

Over the past 30 years, such IMDs have evolved, from relatively bulky, crude, and short-lived devices providing simple stimulation therapies and monitoring functions to complex, long-lived, and miniaturized AIDs, e.g., cardiac IMDs providing a wide variety of pacing and/or cardioversion and defibrillation therapies and/or monitoring functions. Numerous other programmable functions have been incorporated including enhanced capacity to detect and discriminate cardiac arrhythmias, to store data and to uplink telemetry data related to arrhythlnia episodes and applied therapies (if any). Moreover, the capability of interrogating stored device data and real time telemetry of physiologic data, e.g. the real time cardiac EGM and blood pressure and the like, have been incorporated into such IMDs.

Over the same time period, numerous improvements have been made in leads and sensors that are attached to the IMDs which provide for more reliable sensing of physiologic signals and delivery of therapies in therapy delivery IMDs. For example. improved pacing and sensing leads and cardioversion/defibrillation leads and electrodes that have enabled sensing the atrial and ventricular EGM and the delivery of pacing and cardioversion/defibrillation energy at specific selected upper and lower heart chambers. These improvements have led to dramatic reductions in the delivered pacing and shock energy required to capture and cardiovert or defibrillate a heart chamber, respectively. Moreover, in ICD IPGs, the high voltage output circuitry has been improved in many respects to provide monophasic, biphasic, or multi-phase cardioversion/defibrillation shock or pulse waveforms that are efficacious, sometimes with particular combinations of cardioversion/defibrillation electrodes, in lowering the required shock energy to cardiovert or defibrillate the heart.

The earliest implantable pacemaker IPGs employed very simple analog circuit oscillators formed by discrete transistors and other circuit components and were very short-lived and electrically inefficient. The incorporation of digital discrete ICs for logic and memory functions arrayed on circuit substrates and forms of circuit boards enabled higher electrical efficiency and set the stage for the development of more sophisticated operating functions, programmability of operating modes and parameters, data storage and telemetry of stored data as embodied in the MEDTRONIC® SPECTRAX® pacemaker IPGs. Throughout the course of development of these improvements, successive generations of such IMDs have incorporated improved, miniaturized electronic ICs and circuit boards that are powered by long-lived, low current output, low voltage batteries. Most recently, a wide number of IMD system architectures have been developed that incorporate custom microcomputers comprising a microprocessor, RAM and ROM and related elements of a typical microcomputer and other control logic, memory and signal processing circuitry. Such system architectures typically are embodied in two or more ICs that are mounted to a substrate and electrically coupled together. Certain of the ICs are formed by CMOS semiconductor fabrication and others are formed by bipolar semiconductor fabrication.

It is widely understood that such IMDs need to be small enough to be comfortably implanted subcutaneously without being unduly uncomfortable to the patient or cosmetically apparent and must be energy efficient enough to function reliably for many years.

Semiconductor ICs can be designed to be highly energy efficient, but the energy efficiency of ICs that are fabricated to the same design and using the same wafer fabrication process can vary considerably due to unavoidable variations in transistor switching characteristics including nodal capacitance. The electrical power required to operate any given IC in a batch at a specified clock speed, for example, can vary widely due to these variations. Because of the variability in CMOS IC power requirements to operate at a specified speed, it has been necessary to rigorously specify the IC performance and to then test and select ICs provided by vendors under an assumed operating voltage and current.

The typical IMD battery source is limited both in voltage and current output and is usually rated in terms of Amp-hours. With respect to CMOS logic ICs employed in IMDs, the useful life of a given battery, and hence the IMD itself, depends on the voltage and cumulative current drain required by the CMOS logic ICs and other powered components.

There are two distinct mechanisms of power dissipation in a typical CMOS logic gate. The first involves the charging of nodal capacitances of both the input and output of the logic gate as the state of the logic gate is switched. In each case, the power dissipation is proportional to the value of the nodal capacitance, the frequency of switching and the square of the supply voltage. The second mechanism is the switching current component due to both pmos and nmos transistors, which comprise a logic gate, simultaneously conducting current as the logic gate transitions output states. This component, typically referred to as "crowbar current", is distinctly different from the current required to switch the nodal capacitances inherent in CMOS logic gates.

The power supply voltage can be reduced to a level that is equal to the sum of the threshold of an n-channel transistor and the threshold of a p-channel transistor. Thus, the crowbar current is effectively eliminated by only one transistor conducting current regardless of the input voltage. Further reduction of the supply voltage will linearly reduce the current required to switch the nodal capacitances but at a cost of the speed at which switching can be accomplished.

However, the point at which the reduction in supply voltage compromises the operation of a CMOS logic gate varies in manufacturing from wafer to wafer and marginally from die to die. The task of completely testing for the lowest supply voltage that does not compromise operation of all logic gates of each IC die is lengthy. It might be theoretically possible to test for the lowest operating supply voltage of each CMOS IC employed in a given IMD and to provide separate regulated power supply voltages to each such IC. However, the cost of doing so during the fabrication of each individual IMD would greatly exceed any benefits in battery longevity that might be gained.

Thus, the typical approach to reducing current drain in CMOS logic ICs is to specify a supply voltage to the IC to a level that guarantees operation of all of the ICs powered by the IMD battery at the specified speed under worst case semiconductor fabrication processing for each such IC. This same approach of specifying a high enough voltage to account for fabrication variances is followed even when only a single such CMOS IC is employed in the IMM system. Therefore, in practice, excessive power may be consumed by the CMOS IC or ICs of the IMD operating system.

It is a principal object of the present invention to avoid the need for such testing and selection, to quickly determine the minimum operating voltage of dies, and to regulate the operating voltage to approach the minimum operating voltage, thereby minimizing current drain regardless of the manufacturing tolerances of each individual IC die.

SUMMARY OF THE INVENTION

The invention is therefore intended to reduce the power consumption of semiconductor circuits that are used in implantable medical devices or other devices where power consumption is a concern.

The invention is preferably realized in a method or apparatus for conserving power in an IMD operating system of the type having at least one IC powered by a battery wherein, in each such IC, a voltage dependent oscillator for providing oscillator output signals at an oscillation frequency dependent upon applied supply voltage to the IC is incorporated into the IC. The voltage dependent oscillator oscillates at an oscillation frequency that is characteristic of the switching speed of all logic circuitry on the IC die that can be attained with the applied supply voltage. Then, in accordance with the invention, the applied supply voltage is regulated so that the oscillation frequency is maintained at no less than a target or desired oscillation frequency or within a desired oscillation frequency range. In this manner, the power supply voltage that is applied to the IC is based directly on the performance (timing characteristics and switching speed) of all logic circuitry of the IC.

In the case where the IMD incorporates more than one such IC configured in this manner, either a common supply voltage is applied to each such IC that is sufficient to maintain a minimum switching speed of all such ICs, or separate supply voltages are derived in the same manner for each one of the ICs.

More specifically, the present invention is realized by steps of and means for: (a) establishing a target oscillation frequency; (b) deriving a supply voltage from said battery; (c) applying the supply voltage to the integrated circuit, thereby causing the voltage dependent oscillator to provide oscillator output signals at an oscillation frequency dependent upon the applied supply voltage; (d) comparing the oscillation frequency of the oscillator output signals to the target oscillation frequency; (e) incrementally increasing the derived supply voltage if the oscillation frequency of the oscillator output signals is less than the target oscillation frequency and repeating steps (b), (c) and (d); (f) incrementally decreasing the derived supply voltage if the oscillation frequency of the oscillator output signals is greater than the target oscillation frequency and repeating steps (b), (c) and (d); and (g) maintaining the derived supply voltage if the oscillation frequency of the oscillator output signals is equal to the target oscillation frequency and repeating steps (b), (c), and (d).

The IMD operating system includes a system clock that provides a fixed clock signal that is independent of the battery voltage over an operating battery voltage range for system timing and control functions. The target oscillation frequency is preferably related to the system clock frequency. All logic gates of the IC or ICs are preferably switched in state within one clock cycle, and the target oscillation frequency is therefore set to be a multiple of the system clock frequency. Preferably, the voltage dependent oscillator is a ring oscillator which outputs the oscillator output signals at an oscillation frequency dependent upon the applied supply voltage.

In order to provide the comparison function, the oscillator output signals are counted, and the oscillator output signal count accumulated over a predetermined number of system clock signals is compared to a target count that is correlated to the desired oscillation frequency. The counts are compared, and the supply voltage is adjusted upward or downward or is maintained the same dependent upon whether the oscillator output signal count falls below or rises above or is equal to the target count (or within a target count range), respectively.

Moreover, the supply voltage adjustment is preferably achieved employing a digitally controlled power supply. The adjustment of the supply voltage is accomplished by calculating a digital voltage from the comparison of the oscillator output signal count to the target count, and storing the digital voltage in a register of the digitally controlled power supply.

The present invention finds particular utility in controlling the performance and power consumption of CMOS ICs. The method and apparatus of the present invention can be operated to provide a continuously adaptive power supply voltage, based directly on the performance requirements of the CMOS logic, to the IC. The regulated power supply voltage can be set low enough to allow operation of CMOS IC logic below the sum of the p-channel and n-channel thresholds, which reduces power consumption while maintaining satisfactory switching speed.

This summary of the invention and the objects, advantages and features thereof have been presented here simply to point out some of the ways that the invention overcomes difficulties presented in the prior art and to distinguish the invention from the prior art in one or more independent way and is not intended to operate in any manner as a limitation on the interpretation of claims that are presented initially in the patent application and that are ultimately granted.

BRIEF DESCRIPTION OF THE DRAWINGS

The foregoing features, objects and advantages of the invention will become apparent to those skilled in the art from the following detailed description of a preferred embodiment, especially when considered in conjunction with the accompanying drawings in which.

DETAILED DESCRIPTION OF THE PREFERRED EMBODIMENTS OF THE INVENTION

The present invention can be implemented in any IMD that employs ICs that are powered by a power supply for providing a therapy and/or monitoring function. The present invention will be described in relation to an ICD IPG operating system design, but it is not intended that the invention be limited to that particular application when it can be advantageously implemented in other ICD IPG operating systems and in operating systems of other IMDs.

Such ICD IPGs typically are formed having a housing that is hermetically sealed and, therefore, is impervious to body fluids, and a connector header for making electrical and mechanical connection with one or more leads bearing pacing, sensing and cardioversion/defibrillation electrodes adapted to be located in or around selected chambers of the heart. The housing is formed of a suitable, body-compatible material approved for medical use, such as titanium and is shaped physiologically so as to avoid sharp edges which might lead to tissue necrosis following implantation. Typically, the housing is formed having major opposed or parallel surfaces joined together by sides enclosing an interior housing chamber or cavity and having electrical feed-throughs extending therethrough and into the connector header. The housing cavity receives the battery(s) and the high voltage (HV) and low voltage (LV) electronic circuitry which can comprise ICs, circuit boards and discrete components, e.g., but not limited to, the step-up transformer and the high voltage output capacitor(s). Although, there is no particular preferred embodiment of such an ICD, FIGS. 1 and 2 depict one form of such an ICD in which the present invention can be advantageously implemented.

Figure 1:
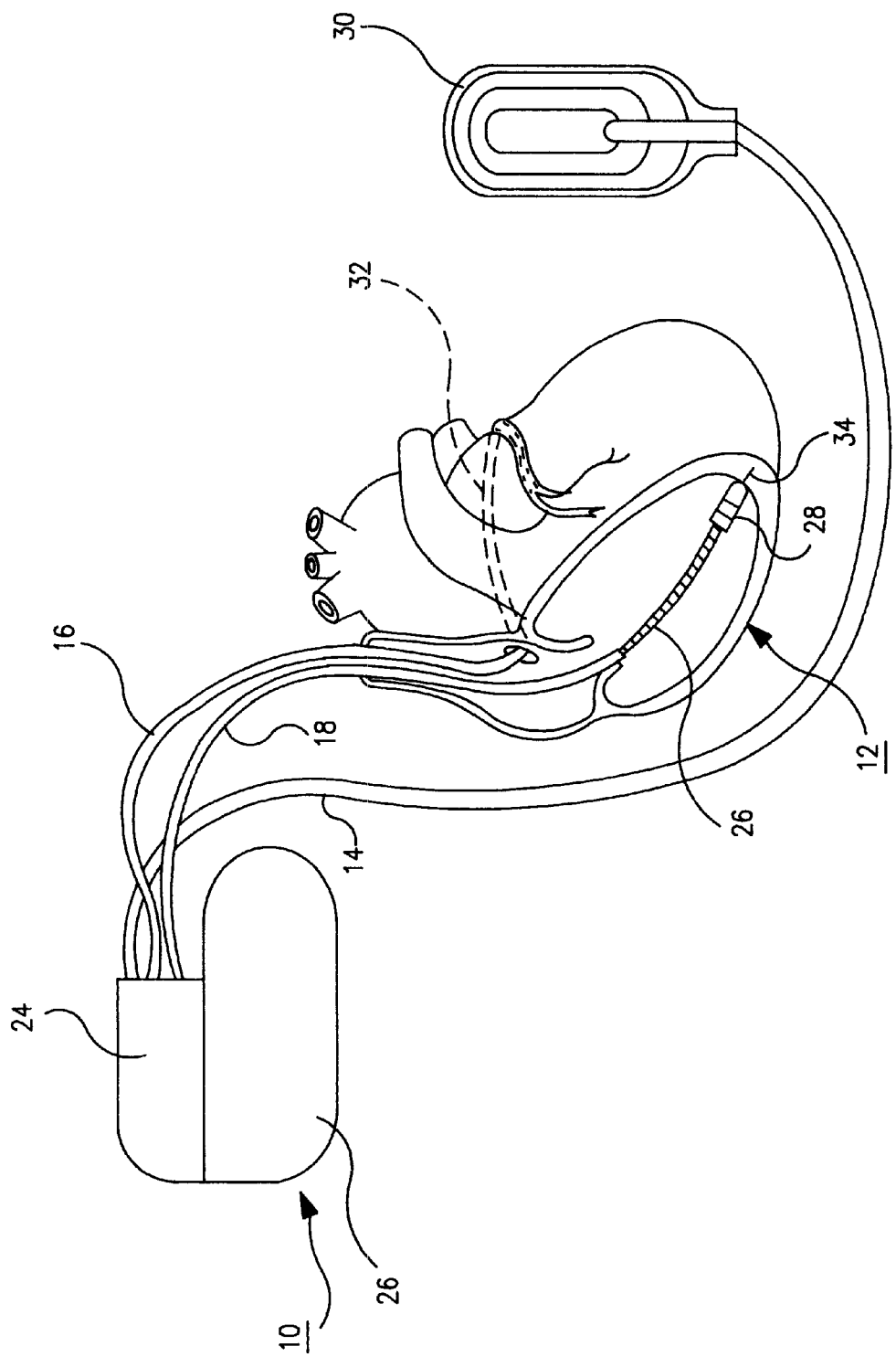
FIG. 1 illustrates the physical components of an ICD IPG and lead system extending to the heart illustrative of a type of IMD in which the present invention may be advantageously practiced.
Figure 2:
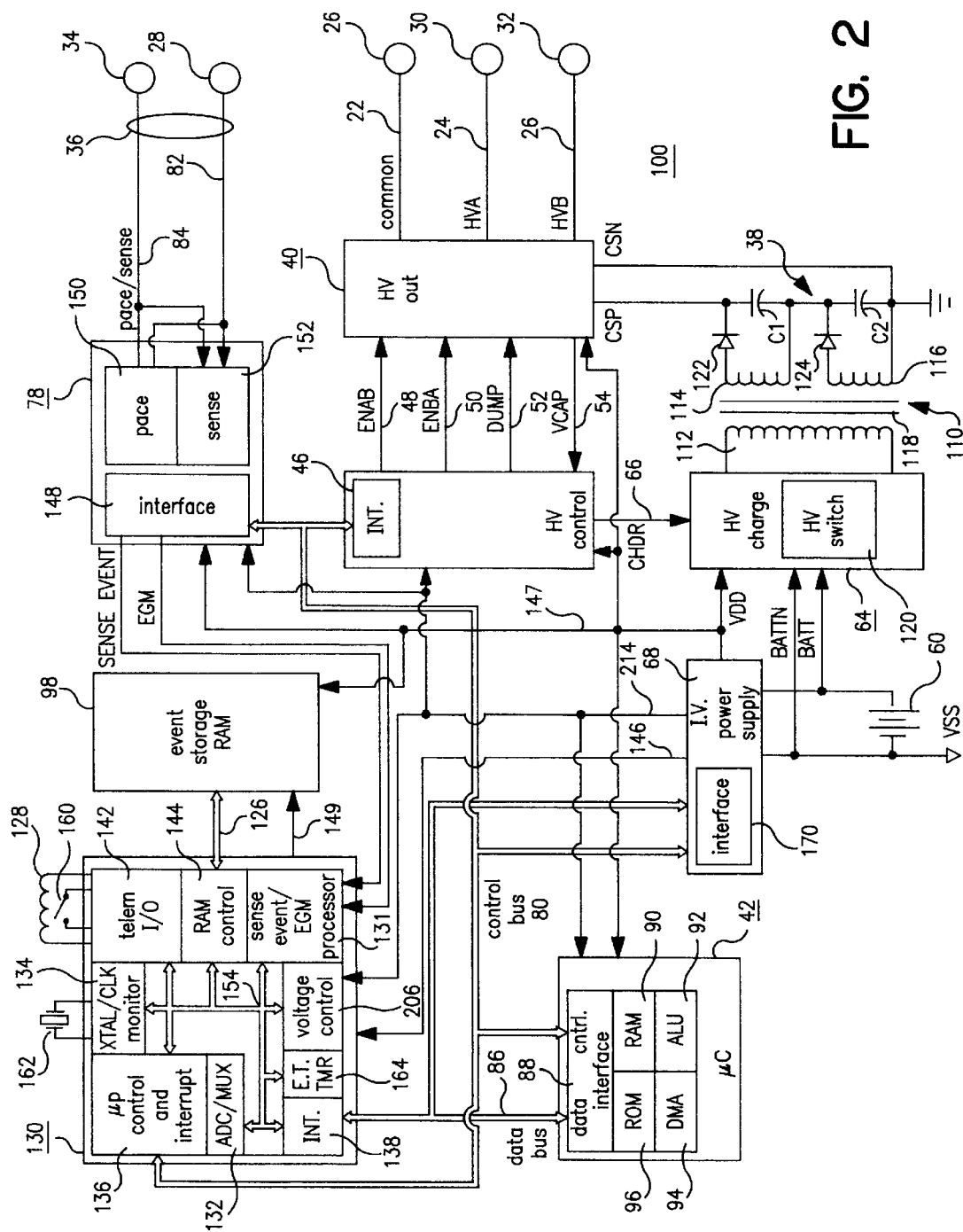
FIG. 2 is a functional block diagram illustrating an ICD system of the ICD IPG of FIG. 1 in which the present invention may be advantageously practiced.

In FIG. 1, an ICD IPG 10 and associated 14, 16 and 18 are illustrated in relation to a patient's heart 12 as in FIG. 1 of commonly assigned U.S. Pat. No. 5,265,588, incorporated herein by reference in its entirety. Over the past 20 years, ICD IPGs have evolved, as described in some detail in, from relatively bulky, crude, and short-lived IPGs simply providing high energy defibrillation shocks to complex, long-lived, and miniaturized IPGs providing a wide variety of pacing, cardioversion and defibrillation therapies. Numerous other programmable functions have been incorporated including enhanced capacity to detect and discriminate cardiac arrhythmias, data storage and uplink telemetry of data related to arrhythmia episodes and applied therapies, provision of staged therapies appropriate to the detected arrhythmia, for example. At the same time, numerous improvements have been made in cardioversion/defibrillation leads and electrodes that have enabled the cardioversion/defibrillation energy to be precisely delivered about selected upper and lower heart chambers and thereby dramatically reducing the delivered shock energy required to cardiovert or defibrillate the heart chamber. The IPG 10 comprises the hermetically sealed, metallic housing 22 and a multi-lumen connector header 24 which contains separate connector blocks and ports for receiving and electrically and mechanically attaching the proximal connector ends of the leads 14, 16 and 18. The feed-throughs (not shown) extend from the connector blocks (not shown) within the connector header 24 and the internal high voltage and low voltage circuitry within the housing 22 in a manner well known in the art.

The cardioversion/defibrillation leads 14, 16 and 18 bear relatively large surface area cardioversion/defibrillation electrodes 30, 32 and 26, respectively that are located in, on or about the heart 12. Cardioversion/defibrillation lead 14 extends subcutaneously and terminates distally in a subcutaneous electrode 30, which is intended to be mounted subcutaneously in the region of the left chest. Cardioversion/defibrillation lead 16 extends transvenously and terminates distally in an elongated coil CS electrode 32 which is located in the coronary sinus and great vein region of the heart 12 and extends around the heart from a point within the opening of the coronary sinus to a point in the vicinity of the left atrial appendage. Ventricular cardioversion/defibrillation lead 18 extends transvenously and is provided with an elongated electrode coil 26 which is located in the right ventricular chamber of the heart 12. Cardioversion/defibrillation shocks can be applied between selected cardioversion/defibrillation electrodes.

The ICD IPG 10 preferably further incorporates atrial and/or ventricular EGM sensing capabilities for detecting atrial and/or ventricular arrhythmias and optionally providing for . Ventricular lead 18 also includes a ventricular pace/sense electrode 34 which takes the form of a helical coil which is screwed into the myocardial tissue of the right ventricle. Lead 18 may also include an additional pace/sense electrode 28 for near field ventricular EGM sensing or a surface electrode on the IPG 10 may be paired with the helical coil electrode 34 for far field ventricular EGM sensing. Additional near field and/or far field atrial EGM sensing and atrial pacing capabilities can be provided using atrial pace/sense electrode pairs on the atrial lead 16 and/or the IPG 10. A more detailed description of the leads illustrated can be found in commonly assigned U.S. Pat. No. 4,932,407, incorporated herein by reference in its entirety. The invention is also believed workable in the context of multiple lead and electrode systems appropriate for the treatment of the patient's arrhythmias.

In the system illustrated, ventricular cardiac pacing pulses are delivered between helical pace/sense electrode 34 and ring electrode 28. Pace/sense electrodes 28 and 34 are also employed to sense EGM signals characteristic of ventricular contractions. As illustrated, it is anticipated that the right ventricular cardioversion/defibrillation electrode 26 will serve as the common electrode during sequential and simultaneous pulse multiple electrode defibrillation regimens. For example, during a simultaneous pulse defibrillation regimen, shocks would simultaneously be delivered between cardioversion/defibrillation electrodes 26 and 30 and between cardioversion/defibrillation electrodes 26 and 32. During sequential pulse defibrillation, it is envisioned that shocks would be delivered sequentially between cardioversion/defibrillation electrodes 30 and 26 and between coronary sinus cardioversion/defibrillation electrode 32 and right ventricular cardioversion/defibrillation electrode 26. Single pulse, two electrode defibrillation pulse regimens may be also provided, typically between right ventricular cardioversion/defibrillation electrode 26 and coronary sinus cardioversion/defibrillation electrode 32.

Alternatively, single pulses may be delivered between cardioversion/defibrillation electrodes 28 and 30. The particular interconnection of the cardioversion/defibrillation electrodes to the ICD IPG 10 will depend somewhat on which specific cardioversion/defibrillation pulse regimen is employed.

The ICD IPG 10 preferably comprises an ICD operating system that provides the operating modes and functions of the MEDTRONIC® GEM 7227 single chamber or GEM DR 7271 dual chamber ICD, IPGs that are programmable in operating mode and parameter values and interrogatable employing the MEDTRONIC® Model 9790C external programmer, for example. FIG. 2 is a functional block diagram illustrating such a single chamber ICD operating system 100 that is merely exemplary of a variety of single chamber and dual chamber ICD systems having all or some of the capabilities described above in which performance based adjustable power supply of the present invention can be advantageously implemented. Basically, all the present invention requires for implementation is a battery 60 and power supply 68 and one or more IC that has an operating speed or other performance variable that depends upon the voltage or power applied to it as described below with respect to FIGS. 3–5. The ICD system 100 includes one of more ICs typically mounted on one or more circuit board and a PC board for mounting a number of discrete components, e.g. telemetry antenna 128, reed switch 160, crystal 162, a set of HV discrete components of the cardioversion/defibrillation sub-system, and the battery 60. If the architecture of the above-incorporated '588 patent depicted in FIG. 3 thereof is employed, the depicted functional blocks and discrete components of FIG. 2 are arranged as part of a LV circuit board, a HV circuit board and a discrete component PC board. However, it will be understood that a single circuit board could be employed that incorporates and supports all of the system ICs. Similar ICD systems to that depicted in FIG. 2 in which the present invention can be implemented are shown, for example, in U.S. Pat. Nos. 4,830,006, 4,693,253, 4,971,058, 5,312,441, and 5,827,326, all incorporated herein by reference in their entireties, for example.

The depicted HV cardioversion/defibrillation therapy delivery sub-system comprises a DC-DC converter powered by battery 60 and which further comprises HV charging circuit 64, a discrete HV step-up transformer 110, the HV output capacitor bank 38, and a HV output or discharge circuit 40 for discharging the charge on the HV output capacitor bank 38 through the cardioversion/defibrillation leads and electrodes of FIG. 1. This sub-system would be incorporated into the HV circuit board and the PC board of the above-incorporated '588 patent architecture, if that architecture were followed. The charge on the HV output capacitor bank 38, comprising series connected capacitors CI and C2 in this case, is selectively discharged through the cardioversion/defibrillation electrodes 26, 30 and 32 coupled via leads 22, 24 and 26 to the HV out circuitry 40.

A typical LV circuit board would incorporate one or more discrete component, IC, data and control buses, interrupt and signal lines, etc., e.g., the LV power supply 68, the pace/sense circuitry 78, the event storage RAM 98, the LV control IC 130, the HV control circuit 44 and the microcomputer 42 and the data bus 86 and control bus 80. Not all of the signal and control lines interconnecting these blocks are shown for simplicity of illustration and because they play no role in the practice of the present invention. In the embodiment of FIG. 2, the LV control IC 130 and the microcomputer 42 can be formed of separate ICs or a single CMOS IC.

The exemplary prior art ICD system 100 of FIG. 2 is powered by the battery 60 coupled to the HV charging circuit 64 and to a LV power supply 68 which provides regulated power to the LV ICs, circuit boards and certain of the discrete components of the system 100. The battery 60 preferably comprises a low voltage, high energy density, higher current output, lithium silver vanadium battery or the like that produces a voltage from about 3.2 volts when fresh to about 2.5 volts at specified end of service. The LV power supply 68 includes the power supply interface 170 and other components described below with reference to FIGS. 3 and 4. The LV power supply generates a regulated supply voltage VDD that is supplied via power line 147 to a number of the illustrated circuits comprising the illustrated microcomputer 42, the pace/sense circuitry 78, off-board RAM 98, the HV control and regulator circuitry 44, the HV charging circuit 64 to power the DC-DC conversion switching circuit 120 and the HV output circuit 40 to power operation of certain switching circuitry therein. The LV power supply 68 also includes a power-on-reset (POR) circuit which provides a POR signal on line 214 to a number of the illustrated circuits to reset logic within those circuits to a known state if a power disruption occurs in a manner well known in the art. In accordance with this illustrated embodiment of the invention, the LV power supply 68 cooperates with the microcomputer 42 and the voltage control circuit 206 to determine and supply minimum necessary power, rather than the regulated power VDD, via power line 146 to certain of the system ICs, specifically the CMOS IC 130.

The operating modes of the ICD system 100 are controlled by the microcomputer 42, the LV CMOS IC 130, and the HV control circuitry 44 following an operating program stored in ROM 96 and RAM 92 which performs all necessary computational and control functions. The microcomputer 42 comprises the typical components of a microcomputer, including the DMA controller 94 and ALU 92 and associated on-board ROM 96 and RAM 90. The program code that governs operation of the ICD system 100 is stored in ROM 96, and the operations are carried out following operating modes and parameters that are stored as operating system data in RAM 90. The operating mode and parameter data is programmable and interrogatable through downlink telemetry programming and interrogation operations that are well known in the art. Such operating modes include the enabling and disabling functions and such operating parameters include pacing pulse width and/or amplitude, sense amplifier sensitivity, event data storage, arrhythmia detection parameters, arrhythmia therapies to be delivered, etc. The ALU 92 performs the logical operations directed by the program code in response to the interrupts and control signals provided by the μP control and interrupt block 136 of LV control IC 130. Data related to the ICD itself, the patient history and the like can also be stored in the RAM 90 for interrogation and telemetry out by the telemetry I/O circuit 142 of LV control IC 130. The DMA 94 provides for direct memory access to register locations in RAM 90, event RAM 98 and ROM 96 without the need for microcomputer control in a manner well known in the art.

A bi-directional control bus 80 and certain discrete interrupt and control lines (not shown) link the input/output interface 88 of microcomputer 42 with input/output interfaces 46, 148, and 170 of HV control circuitry 44, pace/sense circuitry 78, and LV power supply, respectively, and with the microprocessor control and interrupt 136. These on-chip interfaces contain chip-select, address decoding and data bus logic as is typically employed with microprocessor peripherals. The bidirectional data bus 86 and internal bidirectional data and control bus 154 within LV control IC 130 and data bus 126 between event storage RAM allows the microcomputer 42 to control the movement of data between the microcomputer ROM 96 and RAM 90 and registers in event storage RAM 98.

The LV control IC 130 is required to provide inputs to and carry out many of the operations of the microcomputer 42. The LV control IC 130 provides system clock and timing, interrupt, uplink and downlink telemetry functions, ADC/MUX signal processing, sensed event EGM signal processing for arrhythlnia detection and discrimination, event data storage and real-time uplink of the patient's EGM. The system clock is provided by the crystal 162 and crystal oscillator and monitoring circuit 134. The telemetry I/O circuit receives and decodes downlink telemetry interrogation and programming commands when the reed switch is closed by an external programming head magnetic field and downlink telemetry RF signals ring an L-C tank circuit including the telemetry antenna coil 128 and provides the decoded commands to the microcomputer via the data and control bus 154, μP control and interrupt circuit 136 and control bus 80. The telemetry I/O circuit 142 is also triggered by commands from the microcomputer 42 delivered via the reverse path to uplink telemeter stored device, implant, and patient data from the RAM 90 or stored episode EGM data retrieved by RAM control circuit 144 from the event storage RAM 98. The telemetry I/O circuit 142 can also be commanded to uplink telemeter the real time EGM signal processed by EGM sense event/waveform analysis circuit 140 and ADCAMUX 132 provided via internal data and control bus 154. Other system data, including battery voltage, HV capacitor charging time, lead impedance and pace and sensed event markers can also be uplink telemetered via 110 telemetry circuit 142. Such telemetry systems and functions are well known in the art as exemplified by commonly assigned U.S. Pat. No. 5,127,404, incorporated herein by reference.

Pace/sense circuitry 78 of the type described in the above-incorporated '588 patent, for example, includes a pacing pulse generator 150 for generating ventricular pacing pulses, an R-wave sense amplifier 152 for generating sensed event and EGM signals, and an interface 148 and other blanking and high voltage protection circuits. As noted above, dual chamber or single chamber atrial pacing and sensing functions can also or alternatively be provided employing suitable pace/sense circuitry 78 and suitable far field (unipolar) or near field (bipolar) atrial electrode pairs. In the illustrated embodiment, pace/sense circuitry 78 is coupled to ventricular pace/sense electrodes 28 and 34, illustrated in FIG. 1, by means of a conductors 82 and 84 in ventricular lead 36, allowing for bipolar sensing of R-waves and for delivery of bipolar pacing pulses to the ventricle of the heart 12. High voltage protection circuitry is also included in pace/sense circuitry 78 across the conductors 82 and 84 to protect the pacing pulse generator 150 and the sense amplifier 152 from cardioversion/defibrillation shock energy that is picked up on the pace/sense electrodes. The expiration of a pacing escape interval that is timed out in escape interval timer 164 signifies a bradycardia condition, and a pace trigger signal is generated and delivered via control bus 80 to trigger generation of a cardiac pacing pulses by the pacing pulse generator 150. The escape interval is set by the microcomputer 42 based upon a programmed in pacing rate stored in RAM 90 or a physiologic pacing rate in the case where rate responsive pacing capability is provided. A rate responsive pacing function can also be provided in the manner provided in the MEDTRONIC® GEM 7227 single chamber or GEM DR 7271 dual chamber ICD, IPGs.

Moreover, bursts of high rate pacing pulses for treatment of a tachycardia detected by the arrhythmia detection algorithm can also be timed out in the escape interval timer 140 and triggered by pace trigger signals delivered via control bus 80. Sense amplifier blanking intervals following paced and sensed events are specified by microcomputer 42 via control bus 80 and interface 148. It will be understood that the pacing escape interval and the burst pacing intervals can also be established and timed out in the microcomputer 42 rather than in the escape interval timer 140. In that case, the sensed event signal can be conducted to the microcomputer interface 88 via the control bus 80 to reset the escape interval timing by the microcomputer 42.

The sensed event signals indicative of the occurrence of an R-wave (in this illustrated embodiment) are generated by a comparator stage of the sense amplifier 152 which functions by comparing the amplitude of the EGM signal to a sensitivity threshold programmed into RAM 90 by the physician in a manner well known in the art and delivered by microcomputer 42 by means of the data bus 80 and interface 148. The sensed event signals are supplied to the EGM sense event/waveform analysis circuit 140 which outputs a reset signal to the escape interval timer 164 and to the μP control and interrupt circuit 136 via data and control bus 154. The μP control and interrupt circuit 136 via data and control bus 154. responds to the sensed event signals by awakening microcomputer 42 to perform any necessary mathematical calculations, to perform tachycardia and fibrillation detection procedures, and to generate the blanking and refractory intervals.

Moreover, the EGM itself is directed from an amplification stage of the sense amplifier 152 to the EGM sense event/waveform analysis circuit 140. The delivered EGM is sampled and digitized in ADC/MUX 132 and delivered to the RAM control circuit 144 on a continuous basis via internal data and control bus 154. The RAM control circuit cycles EGM data through addressed registers of event storage RAM 98 on a FIFO basis to store a 20 second or so segment of EGM data until tachyarrhythmia detection criteria are satisfied, whereupon the pre-detect data is transferred to permanent storage. The RAM control circuit then stores a post-detect segment of EGM data along with the pre-detect data and an identification of the delivered therapy and response to the delivered therapy for later interrogation and telemetry out in a manner well known in the art.

The tachyarrhythmia detection criteria are specified in ROM 96 and RAM 92 and typically involves elevation of the spontaneous heart rate coupled with other onset, rate acceleration, and stability criteria and various other criteria as described, for example, in the above-incorporated '006, '058, and '441 patents, for example. The spontaneous heart rate is calculated in a heart rate timer maintained by the microcomputer 42, and other characteristics of the EGM are examined to determine whether or not a high rate EGM constitutes a normal sinus rhythm or a malignant tachyarrhythmia. Spontaneous heart rate and EGM width criterion are employed in the MEDTRONIC® GEM 7227 single chamber ICD IPG, and both the atrial and ventricular heart rates and EGMs are examined with information about conduction patterns, regularity and AV dissociation in the detection and classification algorithm employed in GEM DR 7271 dual chamber ICD, IPGs.

When a tachyarrhythmia episode is detected and classified, the appropriate programmed burst pacing therapy or synchronous cardioversion shock therapy or HV defibrillation therapy is delivered. The burst pacing therapy is delivered via pace/sense circuitry 78 as described above. The cardioversion and defibrillation therapies are delivered as follows. In this illustrated embodiment, the HV output circuitry 40 is coupled to the output capacitor bank 38, including capacitors C1 and C2, and is programmable for delivering biphasic cardioversion/defibrillation shocks to selected cardioversion/defibrillation electrodes. The output capacitors C1 and C2 are coupled to secondary windings 114 and 116 of step-up transformer 110 by means of the diodes 122 and 124. The primary winding 112 of step-up transformer 110 is coupled to the HV charging circuitry 64. The HV charging circuitry 64 is controlled by the CHDR signal on line 66 supplied by control circuitry 44 when a malignant arrhythmia subject to cardioversion/defibrillation therapy is detected. The output capacitors C1 and C2 are charged by oscillations of the high frequency, HV transformer 110 in the manner disclosed in detail in the above-incorporated '588 patent. The CSP and CSN voltage across the capacitor bank 38 is monitored and applied via the VCAP signal on line 54 to the control circuitry which detects the point when the VCAP signal level matches the programmed energy level of the cardioversion/defibrillation shock to be delivered. When that condition is satisfied, the control circuitry 44 terminates the CHDR signal and commences the operations to deliver the biphasic cardioversion/defibrillation shock to the selected cardioversion/defibrillation electrodes.

The control circuitry 44 provides three signals of primary importance to the HV output circuitry 40, namely the first control signal ENAB on line 48, the second control signal ENBA on line 50, and the DUMP signal on line 52 which initiates discharge of the charge stored across the output capacitors C1 and C2. The cardioversion/defibrillation electrodes 26, 30 and 32 illustrated in FIG. 1, above, are shown coupled to the output circuitry 40 by means of cardioversion/defibrillation leads 22, 24 and 26. For ease of understanding, these cardioversion/defibrillation leads are also labeled as "COMMON", "HVA" and "HVB". During a logic signal on ENAB, line 48, a cardioversion/defibrillation shock is delivered between electrode 30 and electrode 28. During a logic signal on ENBA, line 50, a cardioversion/defibrillation shock is delivered between cardioversion/defibrillation electrodes 32 and 26. However, other configurations are also possible. For example, subcutaneous cardioversion/defibrillation electrode 30 may be coupled to HVB conductor 26, to allow for a single pulse regimen to be delivered between electrodes 26 and 30. Moreover, the external surface of IPG housing 26 may be exposed and coupled as a remote subcutaneous cardioversion/defibrillation electrode replacing or augmenting the subcutaneous cardioversion/defibrilation electrode 30 and lead 24.

Figure 3:
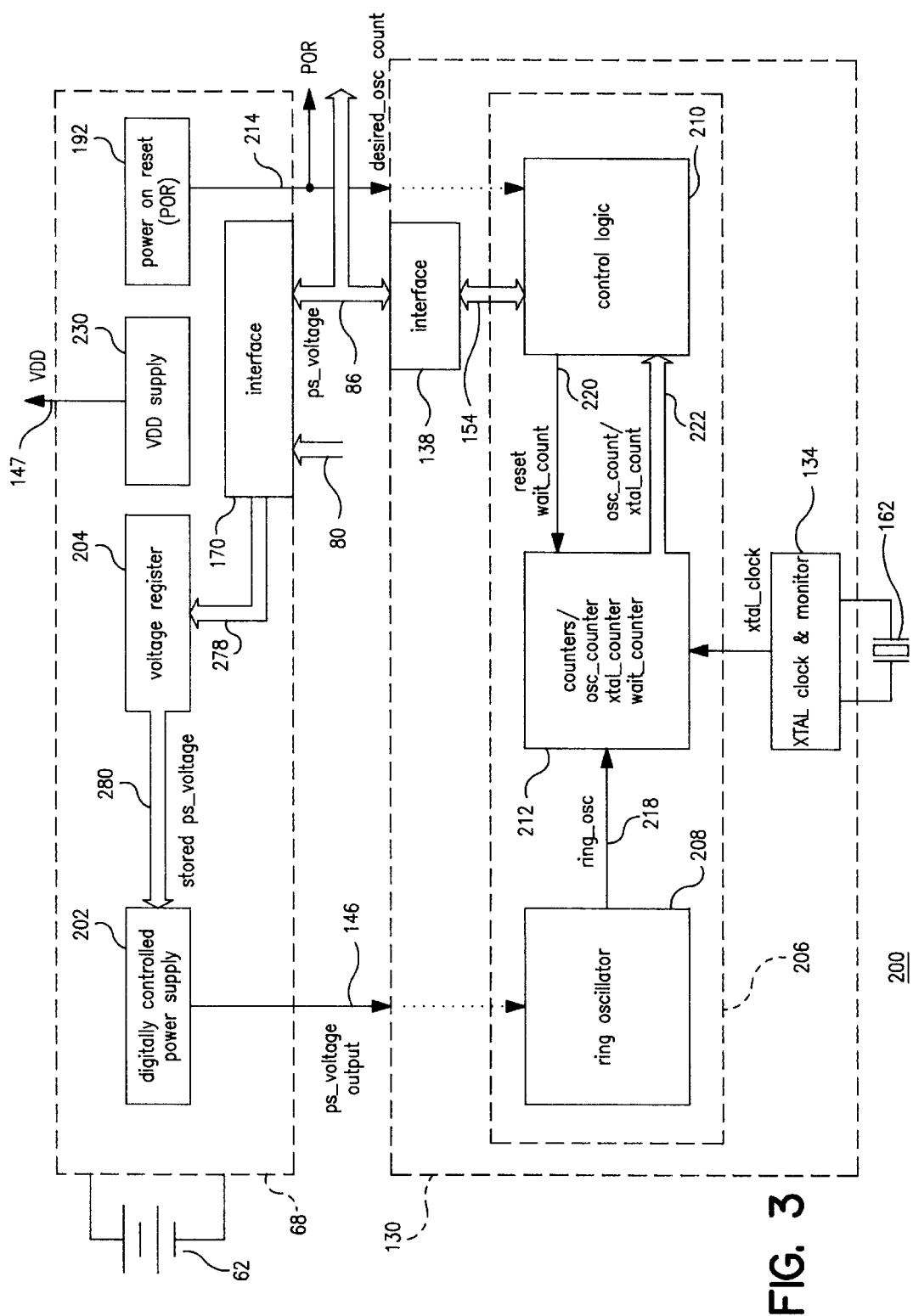
FIG. 3 is a schematic illustration of the power supply control system for powering ICs to function at a minimum operating speed employing custom control logic in accordance with one embodiment of the present invention.

The functions and detailed circuit schematics of the circuitry of FIG. 2 are set forth in the above-incorporated '588 patent. FIGS. 3 and 4a–4b of the '588 patent specifically illustrate the HV circuitry comprising the HV charging circuitry, 64, the Hv output circuit 40 and the HV output transformer 110 and capacitor bank 38. With respect to the charging of the HV output capacitor bank 38, the primary winding 112 is coupled at one terminal to the power supply BATT input terminal through a fuse link and at its other terminal to the BATTN terminal through a duty cycle switching circuit block 120 described specifically in the above-incorporated '588 patent.

The switching circuit 120 includes a power FET transistor having its source and drain terminals coupled across a zener diode in such a fashion that when the power FET is rendered conductive by the CHGDR signal applied at its gate input terminal, it allows current to pass through the primary coil 112 of the HV step-up transformer 110. The power FET preferably has a very low drain-to-source impedance when conductive and a high gate impedance. A zener diode is coupled to the gate terminal of the power FET and has a reverse breakdown voltage of around 10 volts limits the CHGDR voltage. The switching of the power FET on and off effects the charging of the output capacitors C1, C2 in a well known "flyback" fashion. The manner of setting the frequency, duty cycle and amplitude of the CHGDR signal is immaterial to the present invention, and any such manner could be employed. The above-incorporated '588 patent sets forth a desirable way to do so.

All of the timing and control circuits and functions depend upon the voltage and current available from the battery 60, and it is desirable to minimize current drain and voltage depletion to maximize longevity. The cardiac cycle depends on heart rate which can vary in normal sinus function between 50 and 160 bpm in a healthy human heart and can fall below or rise above that range in an unhealthy human heart. Virtually all of the ICD WPG monitoring and bradycardia pacing functions are timed from a sensed cardiac event which depends on the spontaneous heart rate or a pace event at the end of an escape interval timed out during a bradycardia episode. The microcomputer functions can be performed within a few clock cycles of a sensed event or pacing pulse, and then can revert to a low current drain, sleep mode. The continuous EGM sampling, digitizing and storage functions handled by the LV control IC 130 can be completed at 100–200 Hz EGM sampling rates. Thus, current drain is minimized in this context by mini on time of current consuming components.

Most of the ICs employed in the LV circuit boards are fabricated using CMOS fabrication techniques. For example, in FIG. 2, the LV control IC 130 is preferably formed of a single CMOS IC die that performs the functions of the circuits and data and control buses depicted therein. The microcomputer 42 is depicted as formed of a further CMOS IC die, but it may be combined with the LV control IC 130 in a single CMOS IC. As noted at the outset, the variability in CMOS chip operating speed has dictated reliance upon a power supply voltage safety margin that ensures that the desired operating speed can be achieved during a clock cycle. Generally speaking, the ICD operating system clock is established to correlate to the slowest IC circuit switching speed at the regulated power supply voltage to ensure that all the CMOS based logic circuits switch within a clock cycle. For example, the crystal clock and monitor 134 applies power to the crystal 162 and generates a system clock having a frequency of 100 KHz. The clock frequency is relatively insensitive to applied battery voltage due to the function of the crystal 162. It is desired, in accordance with the present invention, to ensure that the supply voltage provided to each CMOS IC be just high enough to provide a sufficient operating speed in order to minimum battery energy consumption in this context.

FIG. 3 is a schematic illustration of a first embodiment of a power supply control system 200, which includes the voltage control circuit 206 of the LV control IC 130 and the LV power supply 68, for powering the LV control IC 130 of FIG. 2 to function at a minimum sufficient operating speed. This system 200 is designed to operate to provide the minimum power supply voltage for the CMOS logic on a given IC die to operate at it's required performance, and the system 200 is therefore replicated for each such IC in the system. The provision of the minimum power supply voltage based on the requirements or performance of each such IC results in lower power consumption than if a fixed voltage power supply incorporating a voltage safety margin is used to power such ICs. In the context of CMOS ICs, the system 200 allows the power supply voltage to be reduced to a value below the sum of the p-channel and n-channel threshold voltages.

System 200 is designed to operate continuously as described below to maintain the IC switching speed within a prescribed range as described further below. However, it will be understood that the system 200 can be triggered to operate less frequently, e.g., once a day. In that variation, the determined supply voltage would have to incorporate a safety margin to account for any fluctuations in voltage required by the powered ICs between the periodic recalculations.

Figure 4:
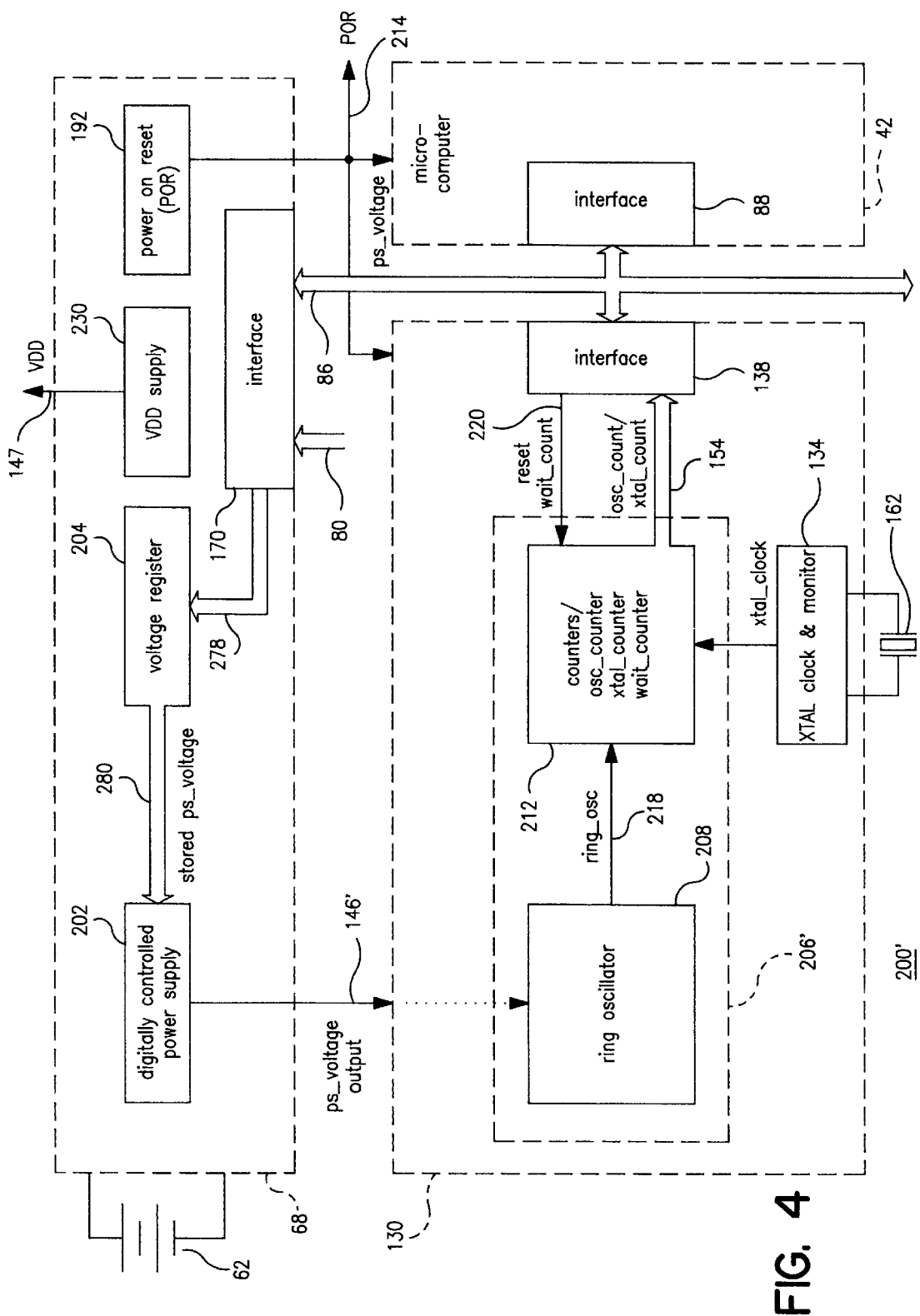
FIG. 4 is an alternate schematic illustration of the power supply control system for powering ICs to function at a minimum operating speed employing software control in accordance with a further embodiment of the present invention.

The LV power supply 68 illustrated in FIG. 3 and in the alternative embodiment of FIG. 4 comprises one or more digitally controlled power supplies 202 that each provide power to a separate CMOS logic IC die, e.g., the LV control IC 130. In each case, the power supply voltage (ps_voltage) is developed in a digitally controlled power supply 202 to match a calculated ps_voltage value stored in digital voltage register 204. The ps voltage value is periodically calculated in control logic 210 of the voltage control circuit 206 as described below and loaded into the digital voltage register 204 via data buses 154 and 86 coupled with the LV IC interface 138 and the power supply interface 170. The ps_voltage output is applied to the voltage control circuit 206 of CMOS logic IC 130 via a dedicated power line 146 to power all gates therein, including those configured as a ring oscillator 208 within the voltage control circuit 206. The ring oscillator 208 is formed of CMOS logic gates, and variations in semiconductor processing or ambient conditions, e.g., ambient temperature, that affect the timing characteristics of the CMOS logic IC will similarly affect the frequency of the ring oscillator 208. The ring oscillator 208 therefore oscillates at a ring_osc frequency that is correlated to the switching speed of all CMOS logic gates on the same CMOS logic ICC die and depends on ps_voltage that is applied to it on power line 146.

The ps_voltage value that is developed in the control logic 210 depends on the frequency of oscillation of the ring oscillator 208 and its comparison to a target or desired frequency range. The target or desired frequency is represented in this embodiment by a desired osc_count that is provided to the control logic 210 from the microcomputer 42 via control bus 86, interface 138, and data and control bus 154, in this case where the control logic 210 is located in the voltage control circuit 206 of the LV control IC 130. The desired osc_count on data and control bus 154 represents the desired switching speed of the CMOS logic gates translated into a number of oscillations of the ring oscillator 208 over a specified number of xtal_clock cycles. The calibration operation performed by the system of FIG. 3 operates continually to account for changes in conditions, e.g., ambient temperature fluctuations, affecting the CMOS switching speed. The POR signal provided on line 214 to the control logic 210 from POR circuit 192, located in the LV power supply 68, functions to reset the control logic 210 to a known state if a power disruption occurs that triggers the POR circuit 192.

Counters circuit 212 of the voltage control circuit 206 comprises an oscillator counter that counts the ring_osc signals generated by ring oscillator 208 on line 218, a wait counter and a xtal_clock pulse counter. The wait-counter in counters block 212 is reset and restarted by a reset wait_count signal on line 220 generated by control logic 210 when the POR signal is detected and each time that a new ps_voltage value is calculated in control logic 210. The wait_counter counts xtal_clock pulses, and the osc_counter and xtal_counter in counters block 212 commence counting the ring_osc signals and the XTAL clock pulses, respectively, when a programmed wait_count is reached. The wait_counter count is established to provide for the settling time of the digitally controlled power supply 202 following a change to a recalculated ps_voltage value stored in voltage register 204 and any disruption in the voltage output from battery 62.

When the wait_count is reached, the control logic 210 receives the osc_count and xtal_count from the counters 212 and compares the osc_count that is accumulated at a predetermined xtal_count to the desired osc_count. The ps_voltage value is recalculated to incrementally increase it if the osc_count is less than the desired osc_count or to incrementally decrease it if the osc_count is greater than the desired osc_count. In this way, the CMOS logic operating speed is incrementally increased or decreased. The wait_count is then reset to time out the power supply settling time and to repeat these calibration operations to determine if the incrementally changed ps_voltage value applied to the ring oscillator 208 causes the incrementally changed CMOS logic switching speed to fall within a desired range represented by upper and lower tolerances of the desired osc_count.

The control logic 210 and counters 212 are preferably implemented in CMOS logic gates that can be specified employing a logic synthesis design methodology, e.g., a Verilog or alternatively a VHDL hardware description restricted to the RTL (Register Transfer Level) subset of the hardware description language. This language is synthesized into logic gates by a software tool such as "Design Compiler", available from Synopsis, Inc., (Mountain View, Calif.). The following Verilog hardware description can be employed in the specification of and fabrication of the control logic 210 and counters 212:

```
/***************************************************************/
/*
                Performance Based Adjustable Power Supply Control Module.

This module converts the ring oscillator output (ring_osc) and the crystal oscillator
    output (clock) into a numerical value (ps_voltage) that is sent to the numerically
    controlled power supply.
      The output value (ps_voltage) is adjusted until the frequency of the ring oscillator
    reaches its desired value. The desired frequency of the ring oscillator is determined by
    simulation of the logic circuits that are powered by the numerically controlled power
    supply. The desired frequency value is assigned to the parameter "desired_osc_count".
```

-continued

The method of adjusting the power supply voltage (ps_voltage) is as follows:
1. A counter (osc_counter) counts the number of oscillations of the ring oscillator.
2. A second counter (xtal_counter) counts the number of oscillations of the crystal oscillator.
3. When "xtal_counter" reaches a predetermined value (sample_count), the value of "osc_counter" is sampled (osc_count_sample).
4. The sampled value (osc_count_sample) is compared to the desired value (desired_osc_count). The comparison is resolved as follows:
    If the sampled value is greater than the desired value, the power supply voltage (ps_voltage) is reduced
    If the sampled value is less than the desired value, the power supply voltage is increased
    If the sampled value is that same as the desired value, the power supply voltage is not changed
5. A third counter (wait_counter) counts until a predetermined time period (wait_count) has expired. This is done to allow the power supply time to settle after its voltage has changed
6  This procedure is then repeated beginning at step 3 above.

```
*/
/*******************************************************************
module aps
    (
        ring_osc,       /* ring oscillator output          */
        POR,            /* Power On Reset                  */
        clock,          /* crystal clock                   */
        ps_voltage      /* power supply voltage            */
    );
/*******************************************************************/
/* I/O                                                              */
input       ring_osc;              /* ring oscillator output     */
input       POR;                   /* Power On Reset             */
input       clock;                 /* crystal clock              */
output [7:0] ps_voltage;           /* power supply voltage       */
/****************************************************/
/* parameters                                                       */
/*
    The parameters below are determined based on the following assumptions:
        The crystal clock frequency is 100 KHz.
        The desired oscillator frequency is 1 MHz.
        The number of crystal clock periods per sample is 20.
        Then the desired oscillator count per sample period will be 200
        (1 MHz./100 KHz. x 20).
    The wait time for the power supply to settle is 1.5 msec.
        (150 crystal clock periods).
*/
parameter [7:0] sample_count       =8'd20;      /* number of crystal clock   */
                                                /* periods per sample        */
parameter [7:0] desired_osc_count  =8'd200;     /* desired oscillator count  */
                                                /* per sample period         */
parameter [7:0] wait_count         =8'd150;     /* number of crystal clock   */
                                                /* cycles to wait while the  */
                                                /* power supply settles      */
parameter [7:0] ps_voltage_init = 8'h80;        /* initial (power on reset)  */
                                                /* value for the power supply*/
                                                /* voltage                   */
/*******************************************************************/
/* registers that becomeflip-flops                                  */
reg [7:0]   wait_counter;      /* counter for waiting until the power   */
                               /* supply has settled                    */
reg [7:0]   xtal_counter;      /* counts the number of crystal clock    */
                               /* cycles                                */
reg [7:0]   osc_counter;       /* counts the number of ring oscillator  */
                               /* clock cycles                          */
reg [7:0]   osc_count_sample;  /* register that holds the ring          */
                               /* oscillator count when it is sampled   */
reg [7:0]   ps_voltage;        /* power supply voltage output           */
reg         end_of_wait;       /* indicates the end of the wait for the */
                               /* power supply to settle                */
reg         end_of_wait_sync;  /* end_of_wait signal synchronized to the*/
                               /* ring oscillator clock                 */
reg         sample_done;       /* indicates the end of the sample period*/
                               /* indicates the time to sample the ring */
                               /* oscillator counter                    */
reg         sample_done_sync;  /* sample_done synchronized to the ring  */
                               /* oscillator clock                      */
reg         sample_done_latch; /* intermediate latch of sample_done_sync*/
                               /* signal to generate sample_done_os     */
reg         sample_done_os;    /* sample_done signal after passing      */
```

```
                                        /* through a one shot based on the ring   */
                                        /* oscillator clock
/*******************************************************/
/* wait counter                                                                   */
/*
counter that is used to wait until the power supply has settled
*/
always @(posedge clock or posedge POR) begin
        if (POR) begin
           wait_counter <= 0;
           end_of_wait <= 0;
        end // if (POR)
        else if (wait_counter == wait_count) begin
           wait_counter <= 0;
           end_of_wait <= 1;
        end // if (wait_counter == wait_count)
        else if (sample_done) begin
           end_of_wait <= 0;
        end // if (sample_done)
        else if (!end_of_wait) begin
           wait_counter <= wait_counter + 1;
        end // if (!end_of_wait)
end // always @ (posedge clock or posedge POR)
/**************************************************************************/
/* xtal counter                                                           */
/*
counts the length of the sample period
*/
always @(posedge clock or posedge POR) begin
        if (POR) begin
           xtal_counter <= 1;
           sample_done <= 0;
        end // if (POR)
        else if (xtal_counter == sample_count) begin
           xtal_counter <= 1;
           sample_done <= 1;
        end // if (xtal_counter == sample_count)
        else if (end_of_wait) begin
           xtal_counter <= xtal_counter + 1;
           sample_done <= 0;
        end // if (end_of_wait)
end // always @ (posedge clock or posedge POR)
/**************************************************************************/
/* ring oscillator counter                                                */
/*
counts the number of ring oscillator cycles
*/
/* synchronize inputs to the ring oscillator counter                      */
/* (end_of_wait and sample_done)                                          */
/*
this is done because the ring oscillator counter has a different clock than the rest of the
logic in this module.
*/
always @(posedge ring_osc or posedge POR) begin
        if (POR) begin
           sample_done_sync <= 0;
           end_of_wait_sync <= 0;
        end // if (POR)
        else begin
           sample_done_sync <= sample_done;
           end_of_wait_sync <= end_of_wait
        end // else: !if (POR)
end // always @ (posedge rin_osc or posedge POR)
/* one shot the sample_done_sync signal based on the ring oscillator clock*/
always @(posedge ring_osc or posedge POR) begin
        if (POR)        sample_done_latch <= 0;
        else            sample_done_latch <= sample_done_sync;
end // always @ (posedge ring_osc or posedge POR)
always @(sample_done_sync or sample_done_latch) begin
        if (sample_done_syn && !sample_done_latch)   sample_done_os = 1;
        else                                          sample_done_os = 0;
end // always @ (sample_done_latch or sample_done_sync)
/* ring oscillator counter */
always @(posedge ring_osc or posedge POR) begin
        if (POR) begin
           osc_counter <= 1;
           osc_count_sample <= 0;
        end // if (POR)
        else if (sample_done_os) begin
```

-continued

```
        osc_count_sample <= osc_counter;
        osc_counter <= 1;
      end // if (sample_done)
      else if (end_of_wait_sync) begin
        osc_counter <= osc_counter + 1;
      end // if (end_of_wait)
end // always @ (posedge ring_osc or posedge POR)
/****************************************************************/
/* power supply voltage adjustment
always @(posedge clock or posedge POR) begin
      if (POR) begin
        ps_voltage <= ps_voltage_init;
      end // if (POR)
      else if (sample_done) begin
        if (osc_count_sample > desired_osc_count) begin
          ps_voltage <= ps_voltage - 1;
        end // if (osc_count_sample > desired_osc_count)
        else if (osc_count_sample < desired_osc_count) begin
          ps_voltage <= ps_voltage + 1;
        end // if (osc_count_sample < desired_osc_count)
        else if (osc_count_sample == desired_osc_count) begin
          ps_voltage <= ps_voltage;
        end // if (osc_count_sample == desired_osc_count)
      end // if (sample_done)
end // always @ (posedge clock or posedge POR)
endmodule // aps
/****************************************************************/
```

Figure 5:
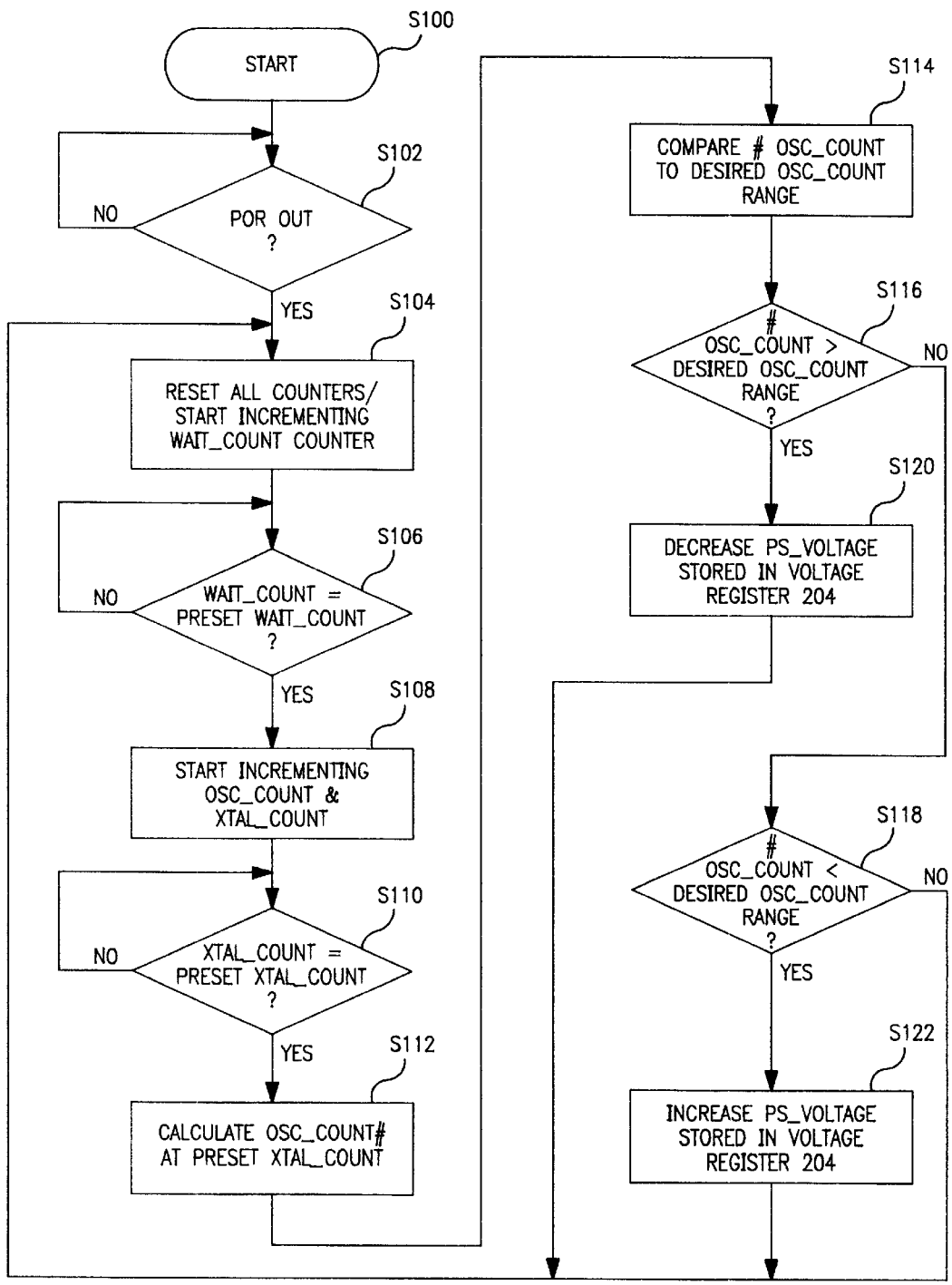
FIG. 5 is a flowchart illustrating the software control of the system of FIG. 4.

FIG. 4 is an alternate schematic illustration of a power supply control system 200' for powering ICs to function at a minimum operating speed employing software control illustrated in FIG. 5 and implemented in ROM in the microcomputer 42 in accordance with a further embodiment of the present invention. In this embodiment, the periodic calculation of the ps_voltage value written into the voltage register 204 is conducted entirely within the microcomputer 42, and the functions of counters 212 can also be conducted by the microcomputer 42 or by hardware counters. The power supply control system 200' otherwise operates in the same manner as the power supply control system 200 of FIG. 3 and can be operated continuously or triggered periodically.

The steps of calculating the ps_voltage value carried out in the power supply control systems of FIG. 3 and 4 are illustrated in FIG. 5. In this illustrated method, a desired osc_count range is defined, although the range can effectively be zero above and below a target or desired osc_count. In step S102, a POR output signal is detected and restarts the wait_count of the wait_count counter and resets the other counters in step S104. The initial POR signal is generated when an IMD battery is first connected to the operating system 100 and may occur from time to time thereafter. The wait_count is also restarted and the other counters are reset in step S104 when steps S120 or S122 are completed. The method steps S104–S122 are continuously repeated in the following manner between POR signals.

In step S 104, the wait_count counter is also incremented by xtal_clock signals, and the accumulated wait_count is monitored in step S106. The osc_count and the xtal_count counters are incremented by ring_osc signals and xtal clock signals, respectively, in step S108, when the wait_count is incremented to the defined wait_count as determined in step S106. The xtal_count is monitored in step S110, and the accumulated osc_count is read by microcomputer 48 or supplied to control logic 210 in step S112 when the incremented xtal_count matches the specified xtal_count. The osc_count is compared to the desired osc_count range by microcomputer 48 or control logic 210 in steps S114–S118.

If the osc_count is greater than the desired osc_count or desired osc_count range as determined in step S116, the ps_voltage level stored in voltage register 204 is decreased in step S120 and step S104 is initiated again. In this way, the derived supply voltage is incrementally decreased if the oscillation frequency of the oscillator output signals is greater than the target or desired oscillation frequency.

If the osc_count is less than the desired osc_count or desired osc_count range as determined in step S118, the ps_voltage level stored in voltage register 204 is increased in step S122 and step S104 is initiated again. In this way, the derived supply voltage is incrementally increased if the oscillation frequency of the oscillator output signals is less than the target or desired oscillation frequency.

The ps_voltage level stored in voltage register 204 is not changed if neither condition of steps S116 and S118 are met and step S104 is initiated again. In this way, the derived supply voltage is maintained if the oscillation frequency of the oscillator output signals is equal to the target or desired oscillation frequency or frequency range.

Thus, the supply voltage regulation of the invention following these steps can be implemented in either hardware or software.

Although the present invention is related in practice to regulating supply voltages for CMOS ICs, it will be understood that its principles may also be applied to other types of semiconductors and circuitry that now exist or may be developed in the future that are affected by supply voltage.

The above described embodiments of the invention can be replicated for each such IC in an IMD so that the power supply supplies separate ps_voltage signals to each such IC. Or a hybrid system can be devised to determine the voltage requirements of all such ICs and to supply a common ps_voltage signal to all such ICs that is sufficient to power the least efficient IC in the IMD operating system.

Although a ring oscillator has been described as the preferred oscillator incorporated into the CMOS IC die, it will be understood that other forms of oscillators that can be implemented using CMOS logic gates and oscillate in dependence upon the gate switching speed can be so incorporated to develop oscillator output signals.

While the present invention has been illustrated and described with particularity in terms of a preferred embodiment, it should be understood that no limitation of the scope of the invention is intended thereby. The scope of the invention is defined only by the claims appended hereto. It should also be understood that variations of the particular embodiment described herein incorporating the principles of the present invention will occur to those of ordinary skill in the art and yet be within the scope of the appended claims.

What is claimed is:

1. Apparatus for conserving power of a battery in an implantable medical device of the type having at least one integrated circuit powered by a supply voltage and current drawn from the battery to operate at an integrated circuit switching speed comprising:

a voltage dependent oscillator incorporated into the integrated circuit for providing oscillator output signals at an oscillation frequency dependent upon the supply voltage applied to the integrated circuit;

means for defining a desired oscillation frequency that is correlated to a desired switching speed of all circuitry of the integrated circuit; and means for regulating the supply voltage to the integrated circuit to maintain the oscillation frequency of the voltage dependent oscillator at the desired oscillation frequency.

2. The apparatus of claim 1, wherein the desired oscillation frequency comprises a desired oscillation frequency range.

3. The apparatus of claim 1, wherein the integrated circuit is formed employing CMOS fabrication techniques into semiconductor elements exhibiting p-channel and n-channel thresholds and the regulating means further comprises:

means for regulating the power supply voltage low enough to allow operation of the CMOS semiconductor elements below the sum of the p-channel and n-channel thresholds, which reduces power consumption while maintaining satisfactory switching speed.

4. The apparatus of claim 1, further comprising:

wait timer means for inhibiting operation of said first timer means for a wait time following provision of the control signal by said control means to allow said power supply means to adjust said supply voltage to a voltage defined by the control signal.

5. The apparatus of claim 1, wherein the desired oscillation frequency comprises a desired oscillation frequency range and the regulating means further comprises:

means for adjusting the supply voltage applied to the integrated circuit;

means for measuring the oscillation frequency and providing a measured oscillation frequency;

means for comparing the measured oscillation frequency to the desired oscillation frequency range;

means for maintaining the supply voltage to the integrated circuit if the measured oscillation frequency falls within the desired oscillation frequency range;

means for increasing the supply voltage to the integrated circuit if the measured oscillation frequency falls below the desired oscillation frequency range; and means for decreasing the supply voltage to the integrated circuit if the measured oscillation frequency rises above the desired oscillation frequency range.

6. The apparatus of claim 1, wherein the regulating means further comprises:

means for adjusting the supply voltage applied to the integrated circuit;

means for measuring the oscillation frequency and providing a measured oscillation frequency;

means for comparing the measured oscillation frequency to the desired oscillation frequency range;

means for maintaining the supply voltage to the integrated circuit if the measured oscillation frequency falls within the desired oscillation frequency range;

means for increasing the supply voltage to the integrated circuit if the measured oscillation frequency falls below the desired oscillation frequency range; and means for decreasing the supply voltage to the integrated circuit if the measured oscillation frequency rises above the desired oscillation frequency range.

7. A method for conserving power in an implantable medical device of the type having at least one integrated circuit powered by a battery comprising the steps of:

(a) forming the integrated circuit with a voltage dependent oscillator for providing oscillator output signals at an oscillation frequency dependent upon applied voltage;

(b) establishing a desired oscillation frequency;

(c) deriving a supply voltage from said battery;

(d) applying the supply voltage to the integrated circuit, thereby causing the voltage dependent oscillator to provide oscillator output signals at an oscillation frequency dependent upon the applied supply voltage;

(e) comparing the oscillation frequency of the oscillator output signals to the desired oscillation frequency;

(f) incrementally increasing the derived supply voltage if the oscillation frequency of the oscillator output signals is less than the desired oscillation frequency and repeating steps (c), (d) and (e);

(g) incrementally decreasing the derived supply voltage if the oscillation frequency of the oscillator output signals is greater than the desired oscillation frequency and repeating steps (c), (d) and (e); and (h) maintaining the derived supply voltage if the oscillation frequency of the oscillator output signals is equal to the desired oscillation frequency and repeating steps (c), (d) and (e).

8. The method of claim 7, wherein the desired oscillation frequency comprises a desired oscillation frequency range.

9. The method of claim 7, wherein the integrated circuit is formed employing CMOS fabrication techniques into semiconductor elements exhibiting p-channel and n-channel thresholds and the desired oscillation frequency is set to ensure that the derived supply voltage allows operation of the CMOS semiconductor elements below the sum of the p-channel and n-channel thresholds, which reduces power consumption while maintaining satisfactory switching speed.

10. The method of claim 7, further comprising the step of:

wait timer means for inhibiting operation of said first timer means for a wait time following provision of the control signal by said control means to allow said power supply means to adjust said supply voltage to a voltage defined by the control signal.

11. Apparatus for conserving power in an implantable medical device of the type having at least one integrated circuit powered by a battery comprising:

a voltage dependent oscillator formed on the integrated circuit for providing oscillator output signals at an oscillation frequency dependent upon applied voltage;

means for establishing a desired oscillation frequency;

means for deriving a supply voltage from said battery;

means for applying the supply voltage to the integrated circuit, thereby causing the voltage dependent oscillator to provide oscillator output signals at an oscillation frequency dependent upon the applied supply voltage;

means for comparing the oscillation frequency of the oscillator output signals to the desired oscillation frequency;

means for incrementally increasing the derived supply voltage if the oscillation frequency of the oscillator output signals is less than the desired oscillation frequency;

means for incrementally decreasing the derived supply voltage if the oscillation frequency of the oscillator output signals is greater than the desired oscillation frequency; and means for maintaining the derived supply voltage if the oscillation frequency of the oscillator output signals is equal to the desired oscillation frequency.

12. The apparatus of claim 11, wherein the integrated circuit is formed employing CMOS fabrication techniques into semiconductor elements exhibiting p-channel and n-channel thresholds and the desired oscillation frequency is set to ensure that the derived supply voltage allows operation of the CMOS semiconductor elements below the sum of the p-channel and n-channel thresholds, which reduces power consumption while maintaining satisfactory switching speed.

13. Apparatus for conserving power in an implantable medical device of the type having at least one integrated circuit powered by a battery comprising:

a voltage dependent oscillator formed on the integrated circuit for providing oscillator output signals at an oscillation frequency dependent upon applied voltage;

power supply means responsive to a control signal for deriving a supply voltage from said battery and applying the supply voltage to the integrated circuit, thereby causing the voltage dependent oscillator to provide oscillator output signals at an oscillation frequency dependent upon the applied supply voltage;

first counter means for counting oscillator output signals and accumulating an oscillator signal count over a predetermined time period; and control means for comparing the oscillator signal count accumulated over the predetermined time period to a desired oscillator signal count representing a desired oscillation frequency of said voltage dependent oscillator and for providing the control signal to the power supply means as a function of the comparison.

14. The apparatus of claim 13, wherein the control means provides said control signal for incrementally increasing the supply voltage if the accumulated oscillator signal count is less than the desired oscillator signal count indicating that the oscillation frequency of the oscillator output signals is less than the desired oscillation frequency.

15. The apparatus of claim 13, wherein the control means provides said control signal for incrementally decreasing the supply voltage if the accumulated oscillator signal count is greater than the desired oscillator signal count indicating that the oscillation frequency of the oscillator output signals is greater than the desired oscillation frequency.

16. The apparatus of claim 13, wherein the control means provides said control signal for maintaining the supply voltage if the accumulated oscillator signal count is equal to the desired oscillator signal count indicating that the oscillation frequency of the oscillator output signals is equal to the desired oscillation frequency.

17. The apparatus of claim 13, further comprising:

means for providing a system clock signal, the frequency of which is independent of supply voltage; and second counter means for counting system clock signals; and wherein:

said control means further comprises means for comparing the oscillator signal count accumulated in the first counter means over the predetermined time period comprising one or more system clock signals counted in said second counter means.

18. The apparatus of claim 13, further comprising:

wait timer means for inhibiting operation of said first timer means for a wait time following provision of the control signal by said control means to allow said power supply means to adjust said supply voltage to a voltage defined by the control signal.

19. The apparatus of claim 13, wherein the integrated circuit is formed employing CMOS fabrication techniques into semiconductor elements exhibiting p-channel and n-channel thresholds and the desired oscillation frequency is set to ensure that the derived supply voltage allows operation of the CMOS semiconductor elements below the sum of the p-channel and n-channel thresholds, which reduces power consumption while maintaining satisfactory switching speed.

\* \* \* \* \*